United States Patent [19]

Tietze

[11] Patent Number: 4,511,844
[45] Date of Patent: Apr. 16, 1985

[54] E-LOG I FIELD COMPUTER

[75] Inventor: Thomas N. Tietze, Kansas City, Mo.

[73] Assignee: Panhandle Eastern Pipe Line Company, Kansas City, Mo.

[21] Appl. No.: 448,818

[22] Filed: Dec. 10, 1982

[51] Int. Cl.³ ............................................. G01N 27/42
[52] U.S. Cl. ..................................... 324/425; 324/71.1; 324/72
[58] Field of Search ............... 324/71.1, 72, 348, 354, 324/425, 65 CR; 361/154; 204/1 T, 404

[56] References Cited

U.S. PATENT DOCUMENTS

| | | | |
|---|---|---|---|
| 2,190,324 | 2/1940 | Peterson | 324/362 |
| 2,344,672 | 3/1944 | Blasier | 324/72 |
| 3,331,021 | 7/1967 | Marsh et al. | 324/71.1 |
| 3,373,100 | 3/1968 | Rubelmann | 204/196 |
| 3,498,900 | 3/1970 | Banks et al. | 204/195 |
| 3,649,492 | 3/1972 | Marsh et al. | 204/148 |
| 3,855,101 | 12/1974 | Wilson | 324/29 |
| 3,909,603 | 9/1975 | Nicolas | 324/11 |
| 3,936,737 | 2/1976 | Jeffries, Sr. | 324/65 CR |
| 3,953,742 | 4/1976 | Anderson et al. | 204/196 |
| 3,999,121 | 12/1976 | Taylor, Jr. | 324/65 CR |
| 4,019,133 | 4/1977 | Manleof et al. | 324/65 CR |
| 4,025,798 | 5/1977 | Siegel | 307/118 |
| 4,051,436 | 9/1977 | Weir, Jr. | 324/102 |
| 4,056,446 | 11/1977 | Vennett | 204/1 T |
| 4,090,170 | 5/1978 | Lincklean-Arriens et al. | 340/5 R |
| 4,095,176 | 6/1978 | Maes et al. | 324/65 CR |
| 4,134,059 | 1/1979 | Stankoff | 324/65 CR |
| 4,157,659 | 6/1979 | Murdock | 73/151 |
| 4,160,171 | 7/1979 | Merrick | 204/195 C |
| 4,160,948 | 7/1979 | Lytgat et al. | 324/65 CR |
| 4,181,882 | 1/1980 | Isaacs et al. | 324/65 CR |
| 4,207,611 | 6/1980 | Gordon | 324/73 R |
| 4,209,376 | 6/1980 | Arita et al. | 204/195 C |
| 4,214,951 | 7/1980 | Bernhardsson et al. | 204/195 C |
| 4,219,807 | 8/1980 | Speck et al. | 324/65 CR |
| 4,258,323 | 3/1981 | Andrews et al. | 324/348 |
| 4,322,805 | 3/1982 | Rog et al. | 324/72 |

Primary Examiner—Michael J. Tokar
Assistant Examiner—Kevin D. O'Shea
Attorney, Agent, or Firm—Litman, Day & McMahon

[57] ABSTRACT

An E-Log I field computer includes a controlled power supply, timers, and a current level stepping relay for circulating cathodic current through a buried metal structure, interrupting the current to allow the decay of residual polarization of the structure and electrolytes within the surrounding ground, and measuring the circulated current and the voltage of structure relative to the ground. The circulated current, voltage of the structure to the ground, and other parameters of interest, such as, the output voltage of the power supply are printed. Then the current level is increased by the stepping relay, and the process is repeated. When a sufficient number of readings have been taken, the data is plotted as a semi-log graph, resulting in an E-log I curve from which the corrosion current and therefore the cathodic protection voltage can be determined.

12 Claims, 5 Drawing Figures

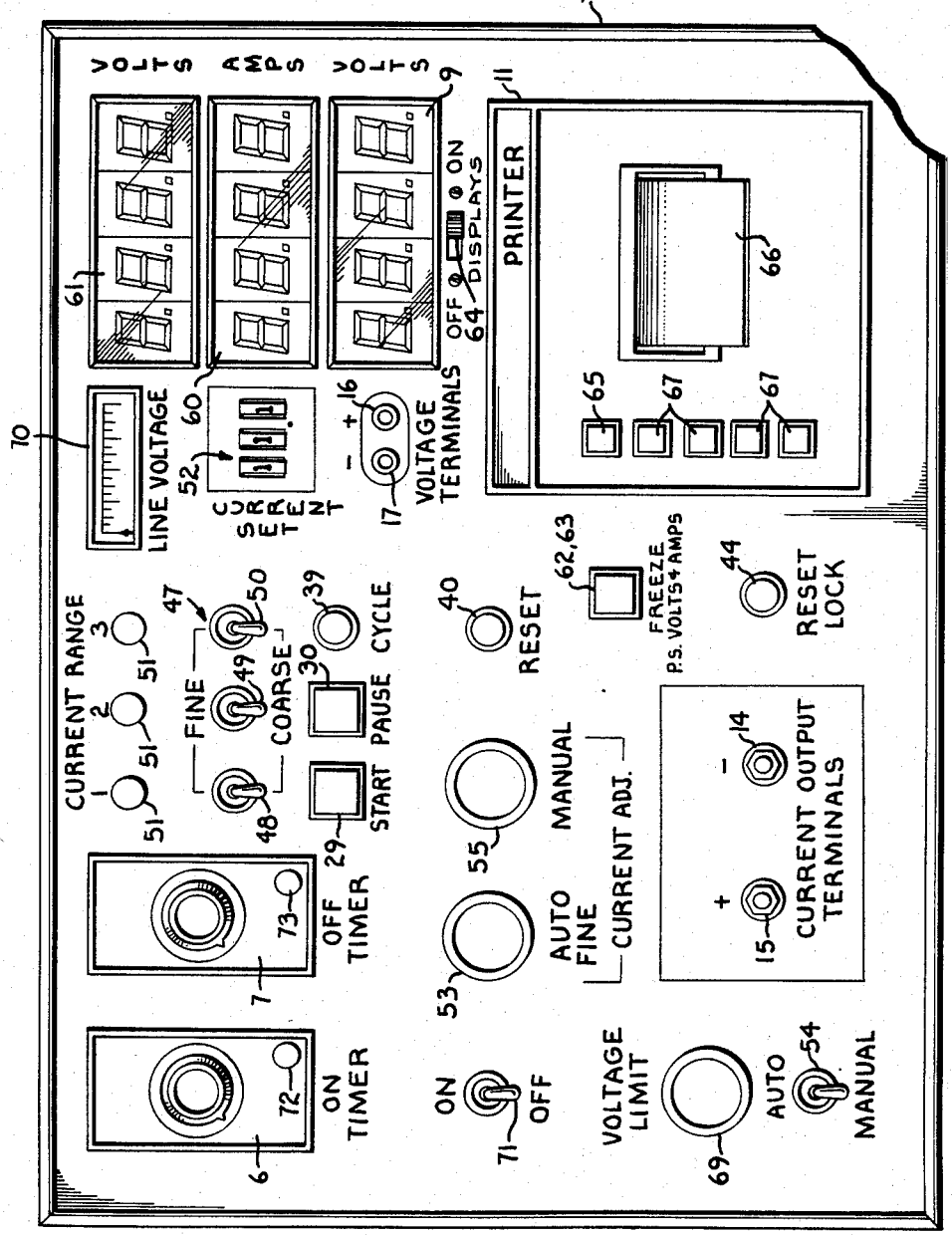

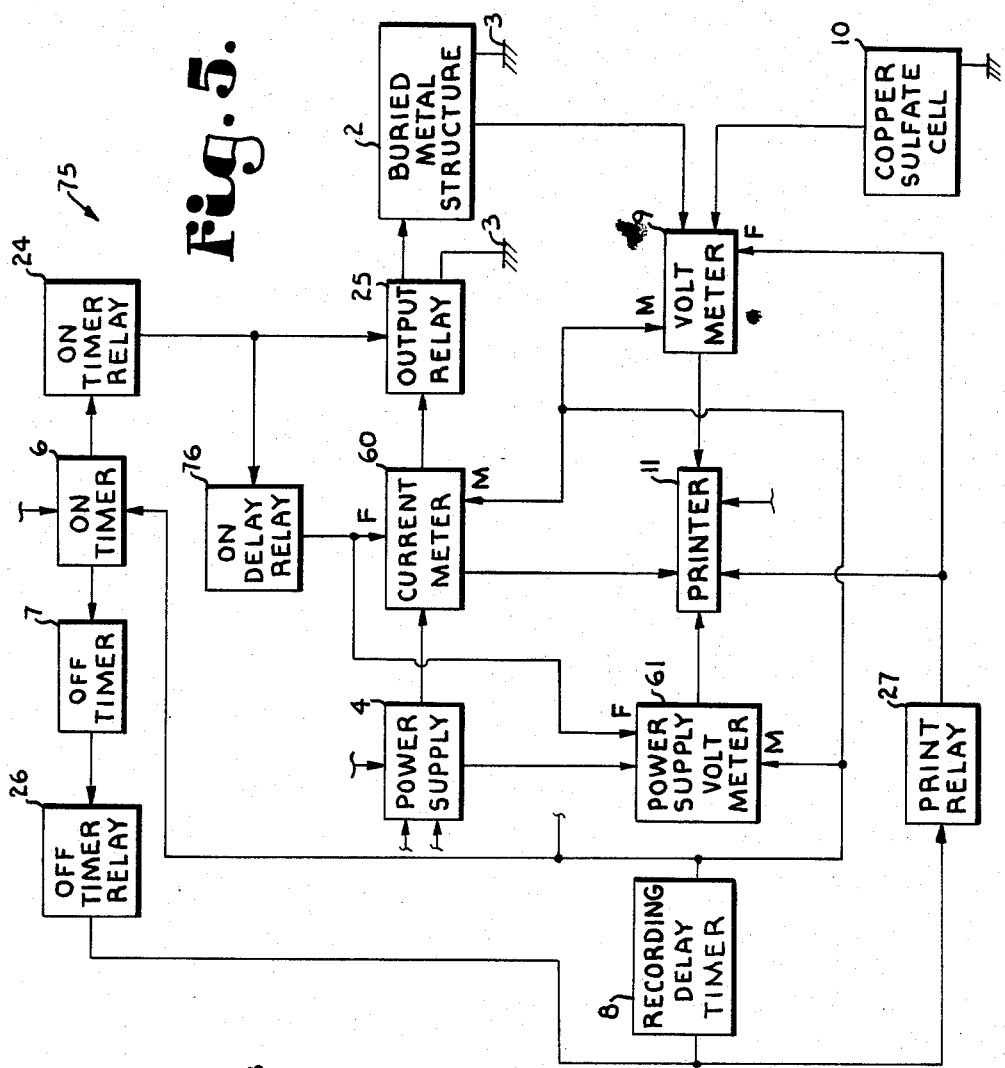
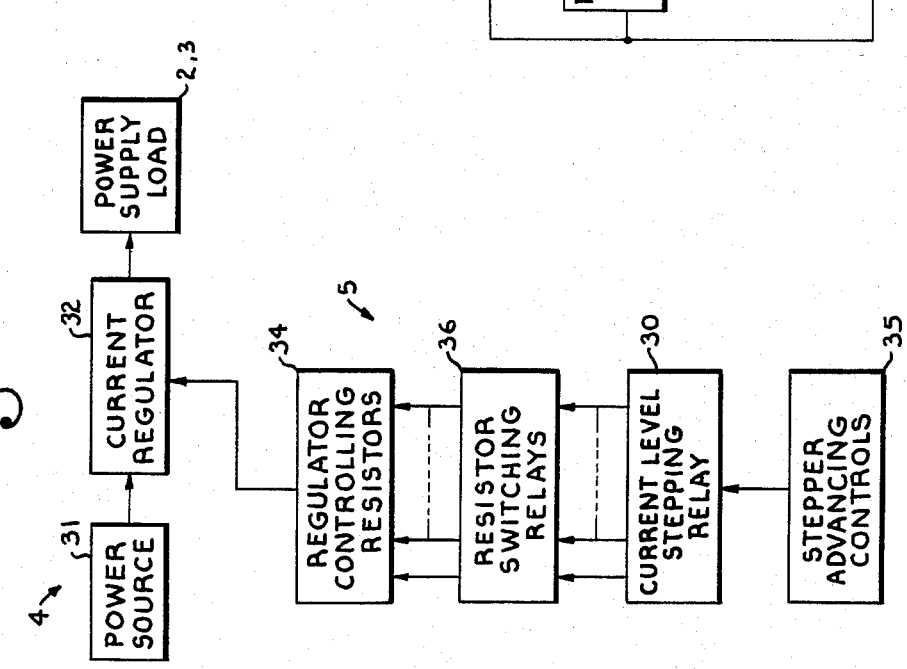

E-LOG I FIELD COMPUTER

FIELD OF THE INVENTION

The present invention relates to the cathodic protection of buried metal structures and, more particularly, to an apparatus for automatically developing data for plotting an E-log I curve to determine the cathodic protection voltage or current requirements of a buried structure.

DESCRIPTION OF THE PRIOR ART

It is well known that buried metal structures, such as steel oil well casings and pipe lines, are subject to corrosion as a result of the electrochemical relationships of the metals thereof with respect to the ground and the electrolytes and moisture therein. Two conventional approaches to preventing the corrosion of such structures are the use of so-called sacrificial anodes and the impression of a voltage across the structure and ground. In each case, the structure to be protected is made cathodic, that is, given a negative potential, with respect to the ground. There is a specific voltage which is optimum for a cathodic protection of a structure in a given type of environment. If the voltage is too low, the structure will not be adequately protected from the corrosion mechanism. Conversely, too high a voltage is uneconomical and may promote other types of corrosion reactions.

One of the methods for determining the optimum cathodic protection voltage is the "E-log I" test wherein cyclically increasing current levels are circulated through the current structure and ground, interrupted for a selected time interval, and then the voltage between the structure and a reference electrode, such as a copper-copper sulfate cell is measured. The voltages are plotted on a linear vertical scale of a graph while the corresponding current levels are plotted on a logarithmic horizontal scale of a semi-log graph. Certain characteristics of the E-log I curve are used to graphically determine the optimum cathodic protection voltage. One disadvantage of the E-log I method is that because of the time dependency of the sequence of measurements and the repetitiveness of the measurements, a well coordinated team effort is required to obtain reliable and consistent results. In particular, unless the time interval between the interruption of circulated current and the measurement of the structure voltage is consistent, the resultant data obtained is unreliable.

SUMMARY OF THE INVENTION

The present invention overcomes many of the complexities of plotting an E-log I curve by automating the steps involved in obtaining the data for plotting such a curve. An apparatus is provided which circulates the current for a timed interval, interrupts the current, times a waiting interval, freezes the reading on a volt meter, and records the voltage reading by printing same on a tape opposite the value of the circulated current. By automating the repetitive steps and timing the interruption-measurement interval, it is only necessary that the apparatus be connected properly whereafter a relatively unskilled crew can produce consistent and reliable results.

OBJECTS OF THE INVENTION

The principle objects of the present invention are: to provide an apparatus for determining the cathodic protection voltage required to protect a buried metal structure from electrochemical corrosion; to provide such an apparatus particularly for developing data to plot an E-log I curve to graphically determine the required cathodic protection voltage of a structure buried in a given soil environment; to provide such an apparatus which circulates a level of current through the structure, interrupts the current, measures the voltage between the structure and a reference electrode at a selected interval after the interruption of the current, prints the voltage and current, and advances to the next level of current; to provide such an apparatus wherein the time interval between interruption of the current and measurement of the structure voltage is consistent for accuracy and repeatability; to provide such an apparatus which derives data in such a manner that the apparatus could be interfaced with a general purpose type computer for computer plotting of the data or computer solution of the cathodic protection voltage; to provide such an apparatus which employs digital current and voltage meters having a storage capability; to provide such an apparatus which is portable for field use; to provide such an apparatus which is rugged enough to perform accurately and withstand use in oil field conditions and other harsh environments; and to provide such an apparatus which is economical to manufacture, accurate and consistent in operation, durable in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a front elevational view of a control panel of the E-log I field computer according to the present invention.

FIG. 2 is a diagramatic view illustrating the manner of connection of the E-log I field computer to a buried metal structure, a reference electrode, and the earth.

FIG. 4 is a block diagram illustrating details of the current level stepper of the E-log I computer.

FIG. 5 is a fragmentary block diagram illustrating a second embodiment of the E-log I field computer according to the present invention.

DETAILED DESCRIPTION OF THE PREFERRED EMBODIMENT

Figure 3:
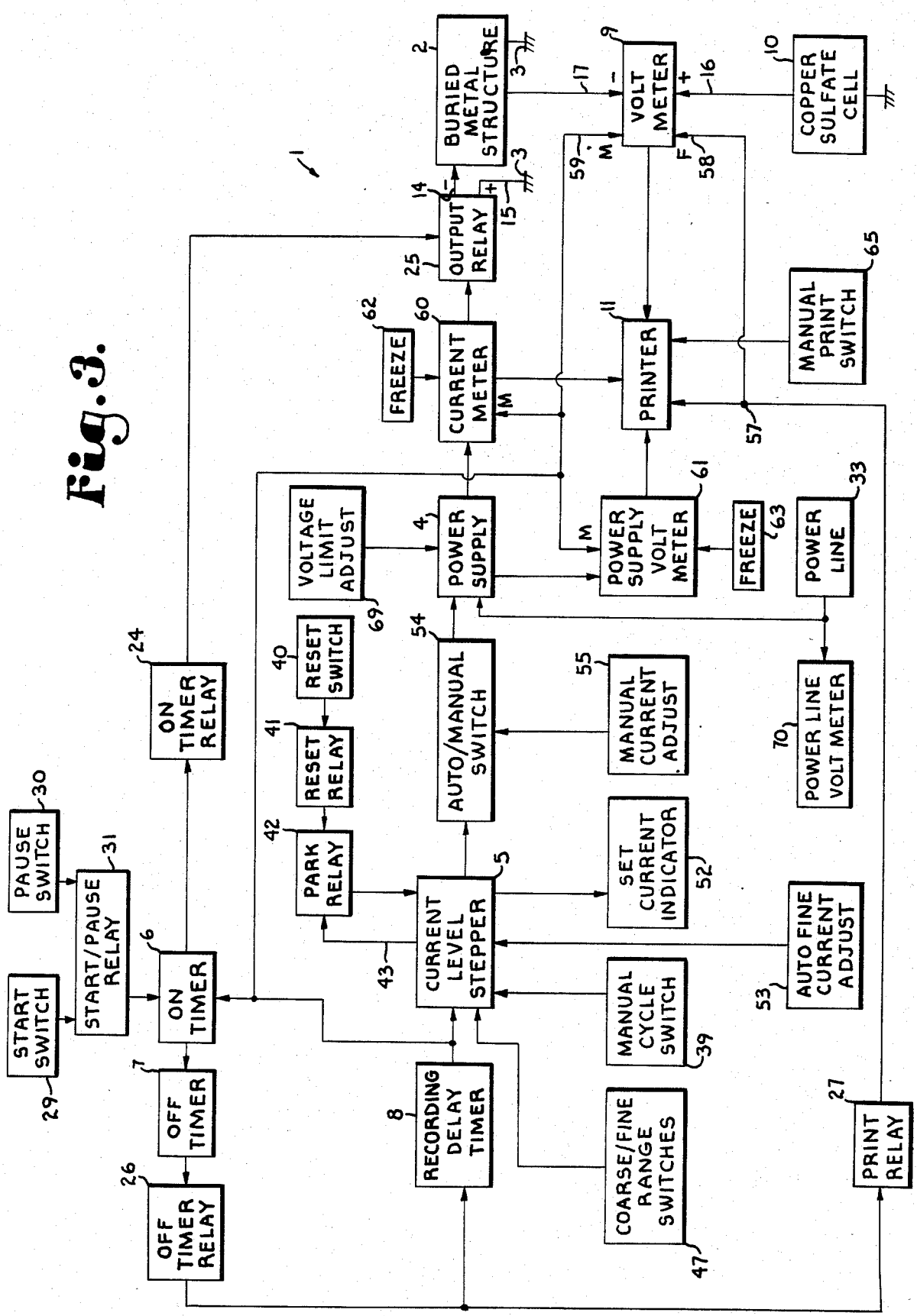
FIG. 3 is a block diagram illustrating the functional components of the embodiment of the E-log I field computer.

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates an apparatus for deriving data to plot an E-log I curve to thereby determine a cathodic protection voltage or current level required to protect a metal structure 2 from corrosion due to electrochemical reactions of the structure 2 with the chemicals present in the adjacent ground 3. The apparatus 1 generally includes a power supply 4 (FIG. 3) controlled by a current level stepper 5 under the influence of an ON timer 6 and an OFF timer 7. Cathodic current from the power supply 4 is circulated through the structure 2 and the ground 3 for an ON timed interval determined by the setting of the ON timer 6. At the end of the ON time interval, the current is interrupted and an OFF timer 7 is actuated. A recording delay timer is connected between the OFF timer 7 and the current level stepper 5 and is activated at the end of an OFF time interval of the OFF timer 7. A volt meter 9 is connected between the structure 2 and the ground 3 by means of the reference electrode, such as a copper-copper sulfate cell 10. The volt meter 9 has an output connected to a printer 11 and makes available thereto a measured voltage reading. Simultaneous with the activation of the recording delay timer 8, the printer 11 is actuated to print the voltage reading from the volt meter 9 in addition to the value of the previously circulated current. At the end of a recording delay interval of the timer 8, the current level stepper 5 is advanced to thereby cause the power supply 4 to provide the next level of current for circulation. As the stepper 5 is advanced, the ON timer 6 is reactivated such that the next level of current is circulated by the power supply through the structure 2 and ground 3. The cycle is repeated until the last level of current has been circulated, interrupted, and the voltage of the structure 2 measured.

The power supply 4, which is a direct current power supply, has the cathode or negative terminal 14 thereof connected to the structure 2 and the anode or positive terminal 15 connected to the ground 3 at a point from 200 to 300 feet from the structure 2 by means of a ground bed which may consist of a quantity of scrap steel buried at a suitable depth. The structure voltage is measured between the structure 2 and the reference electrode 10 which is connected to the ground 3 at a point from 200 to 600 feet from the structure. The volt meter 9 is connected with the positive terminal 16 connected to the reference electrode 10 and the negative terminal 17 connected to the structure 2. As connected, the potential of the structure 2 is below ground potential, that is negative.

It would be possible to connect the volt meter 9 directly to the ground 3 by means such as a steel stake. However, such a manner of connection would add another unkown into the determination, since the electrochemical relation of the stake with the particular soil chemistry would have to be determined and considered along with the relationship of the structure 2 and the ground. More specifically, as the level of the circulated current changed, the voltage between the ground and such a stake would change in much the same manner as the voltage between the structure 2 and the ground changes whereby the voltage reading on the meter 9 would include the voltage between the ground and the stake. Such a voltage would not necessarily be constant as the current changed. For this reason, standard reference electrodes are generally employed. One such reference electrode is the copper sulfate cell, more properly termed a saturated copper-copper sulfate cell which consists of a nonconductive cylindrical tube 19 having a centered solid copper rod 20 and which is closed at the lower end by a porous plug 21 such as of wood or a porous ceramic. The cell is filled with a saturated copper sulfate solution and is placed in a shallow hole in the ground with soil loosely packed against the wall of the tube, and with the soil flooded with water. The positive terminal 16 of the volt meter 9 is connected to the copper rod 20.

In contrast to a field stake, the electrochemical relationship of the copper sulfate cell with the ground is constant. Therefore, the effect of measuring the structure voltage by way of the copper sulfate cell is that the E-log I curve is translated in the direction of the voltage axis and not otherwise distorted. The potential of the copper sulfate cell is known and may be simply subtracted from each voltage reading to result in an E-log I curve from which a cathodic protection voltage or current is to be derived.

Referring to FIG. 3, the ON timer 6 controls the application of the power supply current to the structure 2 by means of an ON timer relay 24 and an output relay 25. In a similar manner, the OFF timer 7 actuates the recording delay timer 8 and printer 11 by means of an OFF timer relay 26. A print relay 27 is connected between the OFF timer relay 26 and the printer 11. Conceivably, the timers 6 and 7 may be provided with relay contact sets internally such that the relays 24, 26 and 27 would not be necessary. The ON timer 6 is actuated externally by means of a start switch 29 and a pause or stop switch 30 operating through a start/pause relay 31.

The illustrated timers 6 and 7 are adjustable, the ON timer 6 being adjustable between zero and ten minutes, and the OFF timer being adjustable between one and six seconds. While the illustrated timers 6 and 7 are electromechanical, solid state timers could also be employed.

During an ON time interval of the ON timer 6, the timer 6 closes and maintains closed contacts (not shown) which energize the ON timer relay 24 to cause the output relay 25 to apply the power supply current to the structure 2. At the end of the ON interval, the ON timer 6 opens the contacts which control the ON timer relay 24 thereby interrupting the circulation of power supply current and closes contacts which activate the OFF timer 7. During the OFF interval no switching action takes place within the apparatus 1. At the end of the OFF interval, contacts of the OFF timer 7 are closed to thereby activate the OFF timer relay 26. The OFF timer relay 26 in turn closes contacts which activate the recording delay timer 8 and the print relay 27. The recording delay timer 8 is provided to delay the advancement of the stepper 5 to thereby prevent errors in the recording of the volt meter reading because of switching transients in the system. Preferably, the contact closure of the OFF timer relay 26 is momentary, that is, just long enough to activate the timer 8 and relay 27. At the end of a recording delay interval of the timer 8, contacts within the timer 8 are closed to thereby cause the advancement of the stepper 5 to the next current level and the reactivate the ON timer 6.

The current level stepper 5 is operative to cooperate with the power supply 4 to set a series of selected levels of current for circulation through the structure 2 and ground 3. Any type of arrangement which functions to accomplish such objectives could be employed in the apparatus 1. Referring to FIGS. 3 and 4, the illustrated stepper means 5 includes a stepping relay 30, and the power supply 4 includes a power source 31 and a current regulating means or regulator 32. The power source 31 provides direct current and may include a power transformer, rectifiers, and filters (not shown) which are connected to a power line 33 which may be either an electric utility outlet or, in the field, an outlet of a suitable generator. The preferred current regulator 32 is a type wherein the set and maintained current level is determined by the resistance value of one of a plurality of regulator controlling resistors 34 which are interconnected thereto.

The preferred stepping relay 30 is a solenoid advanced multiposition rotary switching unit which is operative to sequentially close a set of contacts in each of a plurality of positions thereof. Each time the stepper advancing controls 35 are actuated, the relay 30 advances to the next set of contacts until the last set of contacts has been closed, at which time the relay 30 returns to a starting position. The closure of a set of contacts in each position is operative to connect one of the regulator controlling resistors 34 to the current regulator 32. Preferably the resistors 34 are not connected to the regulator 32 directly by the stepping relay 30 but indirectly by respective resistor switching relays 36. Since the current output level of the regulator 32 is determined by the resistance connected across the control terminals, measures must by taken to prevent uncontrolled changes in the control resistances such as contact resistance caused by corrosion of the contacts of the stepping relay 30. Therefore, the relays 36 employ non-corrodible contacts such as gold contacts or enclosed mercury wetted contacts.

The stepper advancing controls 35 include the recording delayed timer 8 which is employed during automatic cycling of the stepper 5, a manual cycle switch 39, and a reset switch 40. The reset switch operates through a reset relay 41 to control a park relay 42. The park relay 42 upon activation is operative to repeatably cycle the stepper 5 to the starting position thereof. A feedback connection 43 from one of the contacts in the starting position of the stepper 5 causes deactivation of the park relay 42 when the stepper reaches the starting position thereof. A reset lock switch 44 (FIG. 1) is preferably interconnected with the reset switch 40 such that both switches 40 and 44 must be operated to reset the stepper 5. The purpose of this is to avoid unintended resetting by accidental operation of the reset switch 40 which would necessitate a wait for the resetting process to be completed before readings could be resumed. As the name implys, the manual cycle switch 39 is operative to advance the stepper 5 one position each time the manual cycle switch 39 is operated.

The illustrated stepper 5 is adapted to set levels of current for circulation in 3 ranges: a first range from zero to one ampere in two hundred milliampere (200 ma.) steps; a second range from one to ten amperes in five hundred millampere (500 ma.) steps; and a third range from ten to twenty amperes in one ampere steps. There are situations wherein it is not desirable or necessary to take readings at each of the fine current steps described above. Therefore, the apparatus 1 is provided with coarse-fine range switches 47 including a first range switch 48, a second range switch 49, and a third range switch 50. Placement of any of the range switches 47 in the fine position causes the stepper 5 to sequentially set each of the fine current steps within the corresponding range. Conversely, placement of any of the range switches 47 in the course position causes the stepper 5 to sequentially set every other level of current within the corresponding range. The apparatus 1 may be provided with coarse/fine range indicator lights 51 corresonding to each of the range switches 47 to indicate to an operator the state of the respective range switch.

The apparatus 1 may be adapted to set levels of circulated current which facilitate plotting of the E-log I current, that is, current values which correspond to major divisions of the current axis of the graph paper or other medium employed, such as the current values described above. In this way, only the voltage readings of the volt meter 9 need to be recorded and subsequently plotted on the standardly employed current division lines. Preferably, the current level stepper 5 is provided with a readout device to indicate which current level is being circulated for the convenience of the operator. Such a set current indicator 52 may provide a merely nominal indication of the current level set since other instruments are provided for actually measuring the circulated current level as will be described below. The illustrated current indicator 52 is connected to appropriate terminals of the stepper 5 and is actuated to read out the nominal value of the current set by the stepper 5 in each position thereof. The apparatus 1 is provided with a control for finely adjusting the levels of current set by the stepper 5. The fine current adjustment control 53 provides for correction of the current levels which may vary somewhat from the desired level because of the aging of the components of the stepper 5 and the power supply 4 or for other reasons.

The apparatus 1 includes provisions for setting the levels of current manually. An auto/manual switch 54 is connected between the stepper 5 and the power supply 4. The switch 54 is operable to select either the stepper 5 for automatic setting of the current levels or a manual current adjustment control 55. The start switch 29 and pause switch 30 are used in the manual mode to connect the power supply 4 to the structure 2 and ground 3, to circulate the current, interrupt the current, and record the voltage at the selected interval after interruption of the current.

The volt meter 9 is preferably a digital volt meter with the ability to freeze or hold a reading on command and the ability to output a digital representation of the reading. Such meters are conventionally available. In the apparatus 1, the voltage hold or freeze signal for the volt meter 9 is provided by the print relay 27. The freeze signal causes the meter 9 to cease updating the voltage reading and transfer the digital representation of the reading to the an output register. The output register is connected to the printer 11 by a serial or, preferably, a parallel line such that the representation may be transferred to the printer. The response of the meter 9 in freezing is generally faster than the response of the printer 11 in printing such that both functions can be actuated by the same signal. If necessary, a signal delay device can be connected between the printer 11 and a junction 57 between the printer relay 27 and the lines connected to the printer 11 and volt meter 9. In FIG. 3, the freeze terminal 58 of the meter 9 which receives freeze signal is marked "F". The meter 9 is returned to the measuring mode by a measure signal received at a measure terminal 49 (marked "M"). The measure signal is provided by the recording delay timer 8 at the same time that the ON timer 6 is reactivated.

The apparatus 1 is provided with an ammeter or current meter 60 for measuring the level of circulated current. The illustrated current meter 60 is connected between the power supply 4 and the output relay 25. Alternatively, the meter 60 could be connected between the output relay 25 and either the structure 2 or ground 3. When readings are taken in the manual mode, the current meter 60 may be used to assist the operator in setting the desired level of current for circulation. A power supply volt meter 61 is also preferably provided to measure the output voltage of the power supply 4. The volt meter 61 may be used to assure that the output voltage of the power supply 4 is correct for each level of circulation, for further evaluation of the structure voltage readings, or in combination with the current meter 60 to determine the electrical resistance of the soil. The meters 60 and 61 are digital meters and constructed and operated in a manner similar to the volt meter 9.

The apparatus 1 may include a current meter freeze control 62 for the meter 60 and the power supply volt meter freeze control 63 for the meter 61 to selectively freeze the readings on the respective meters for subsequent printing. The freeze controls 62 and 63 may be implemented as a double pole switch unit such that both of the power supply meters 60 and 61 are frozen at the same time. The readings on the meters 60 and 61 would normally be frozen during the ON time interval when the power supply current is being circulated. The meters 60 and 61 are returned to the measuring mode by the same measure signal which is applied to the volt meter 9 and which is provided by the recording delay timer 8 at the end of the recording interval. The switches 62 and 63 may be connected to toggling circuitry (not shown) such that pressing the switch unit once causes freezing of the meters 60 and 61 and pressing the unit a second time returns the meters to measuring modes thereof. The apparatus 1 may include a display ON/OFF switch 64 for selectively activating or deactivating the read-out displays of the meters 9, 60 and 61.

The printer 11 may be any type of printing unit such as an impact printer or a thermal printer. The printer is normally actuated by the print relay 27 but may include a manual print switch 65 for selectively printing readings of the meters 9, 60, and 61 which are connected thereto. Since the printing functions in the apparatus 1 are limited, the printer 11 may be a narrow format printer which prints on a tape 66 provided on rolls. The printer 11 may include additional switches 67 to control other functions such as advancing, printer disabling to install a roll of tape, and the like.

The power supply 4 may be provided with a voltage limit control 69 to limit the ability of the power supply to raise the output voltage to maintain a constant output current level. In addition, a power line volt meter 70 may be provided for monitoring the incoming voltage from the power line 33. The meter 70 may be an analog type meter. While only one power supply 4 is illustrated in FIG. 3, the apparatus 1 may include separate power supplies for powering the timers, the relays, the displays of the meters, the meters themselves, and the printer. An ON/OFF power switch 71 is operable to connect the power supply 4 and other power supplies of the apparatus 1 to the power line 33. The ON timer 6 and OFF timer 7 are preferably provided with respective indicator lights 72 and 73 to indicate to the operator that the timers are in operation. The apparatus 1 is preferably housed in a sturdy enclosure 74 which is portable and which is rugged enough for use in the field.

FIG. 5 illustrates a second embodiment of the E-log I field computer apparatus according to the present invention. In the apparatus 75, the readings of the current meter 60 and the power supply volt meter 61 are frozen automatically. An ON delay relay 76 is connected to the ON timer relay 24 and is activated at the beginning of the ON time interval of the ON timer 6. At the end of a current hold interval or ON delay interval, which occurs before the end of the ON timer interval, the relay 76 is operative to apply a freeze signal simultaneously to the meters 60 and 61 to thereby freeze the readings thereon. The readings are subsequently printed by the printer 11 during the recording interval of the timer 8 along with the structure voltage reading of the meter 9. The meters 60 and 61 are returned to the measuring modes thereof by the timer 8 at the same time that the ON timer 6 is reactivated. In all other respects, the apparatus 75 is substantially similar to the apparatus 1.

It is to be understood that while certain forms of the present invention have been illustrated and described herein, it is not to be limited to the specific forms or arrangement of parts described and shown.

What is claimed and desired to secure by Letters Patent is as follows:

1. An apparatus for acquiring data to determine the cathodic protection voltage requirement of a buried metal structure comprising:
   (a) power supply means operatively connected to a buried metal structure and the ground in contact with said structure and operable to circulate electrical current therethrough;
   (b) current stepper means operatively connected to said power supply means and operative to set one of a plurality of selected current levels for circulation by said power supply means and to advance to a next current level in response to a stepper advance signal;
   (c) a current meter connected in a circuit loop including said structure, said ground, and said power supply means and operative to measure and indicate the level of the circulated current;
   (d) volt meter means operatively connected between said structure and said ground and operative to measure a structure voltage of said structure relative to said ground corresponding to each level of said circulated current and to releasably retain said structure voltage in response to a voltage hold signal;
   (e) a printer connected to said volt meter means and operative to print each value of said structure voltage which is retained by said volt meter means; and
   (f) timer means operatively connected to said power supply means, said current stepper means, said printer, and said volt meter means and operative to effect in a repeating sequence: the circulation of said current for an ON interval of selected duration; the interruption of said current for an OFF interval of selected duration; the provision of a voltage hold signal to said volt meter means to cause the retention of a structure voltage corresponding to the previously circulated current level and the printing of the retained structure voltage at the end of said OFF interval; the release of said volt meter means from retaining said structure voltage after the printing thereof; and the provision of said stepper advance signal to cause the advancement of said current stepper means to said next current level whereby a plurality of circulated current levels and corresponding structure voltage levels are obtained for plotting a graph to determine the cathodic protection requirements of said structure in said ground.

2. An apparatus as set forth in claim 1 wherein:
(a) said current meter is operative to releasably retain the value of the circulated current in response to a current hold signal;
(b) said current meter is connected to said timer means and receives therefrom said current hold signal during said ON interval;
(c) said current meter is connected to said printer which prints at the end of said OFF interval the value of circulated current which is retained by said current meter; and
(d) said current meter is released from retaining said value of circulated current by said timer means after the printing thereof.

3. An apparatus as set forth in claim 1 wherein:
(a) said power supply means includes a current regulator which maintains a current level determined by the resistance of a resistor connected to control terminals of said regulator;
(b) said current stepper means includes a plurality of resistors for setting respective levels of said circulated current; and
(c) said stepper means is operative to effect the connection of a respective one of said resistors to said regulator each time said stepper advance signal is provided by said timer means.

4. An apparatus as set forth in claim 3 wherein said current stepper means includes a stepping relay.

5. An apparatus as set forth in claim 1 wherein:
(a) said timer means includes an ON timer, an OFF timer, and a recording delay timer;
(b) said ON timer is operatively connected to said power supply means and upon activation effects said circulation of said current for said ON interval and the interruption of said current at the end of said ON interval;
(c) said OFF timer is operatively connected to said volt meter means and said ON timer, is activated by said ON timer at the end of said ON interval, and effects the retention of said structure voltage at the end of said OFF interval by providing said voltge hold signal to said volt meter means;
(d) said printer is operatively connected to said OFF timer and is activated thereby at the end of said OFF interval to print the value of said structure voltage which is retained by said volt meter means; and
(e) said recording delay timer is operatively connected to said ON timer, said OFF timer, said current stepping means, and said volt meter means and is activated by said OFF timer at the end of a recording interval of selected duration to effect: the activation of said ON timer; the advancement of said current stepper means to the next current level by providing said stepper advance signal thereto; and the release of said volt meter means from retaining the previously measured structure voltage thereby allowing said volt meter means to measure a structure voltage associated with said next current level.

6. An apparatus as set forth in claim 5 including:
(a) said current meter being operative to releasably retain the value of said circulated current measured thereby in response to a current hold signal;
(b) an ON delay timer operatively connected between said ON timer and said current meter and being operative to provide said current hold signal to said current meter after a current hold interval of selected duration following the activation of said ON timer;
(c) said current meter being connected to said printer whereby siad printer prints the value of said circulated current which is retained by said current meter during said recording interval; and
(d) said current meter being connected to said recording delay timer whereby said current meter is released for retaining said value of circulated current at the end of said recording interval thereby allowing said current meter to measure a next current level.

7. An apparatus as set forth in claim 6 including:
(a) a power supply volt meter connected to said power supply means and said ON delay timer and operative to releasably retain the power supply voltage of said power supply means in response to said current hold signal;
(b) said power supply volt meter being connected to said printer for printing the value of said power supply voltage during said recording interval; and
(c) said power supply volt meter being connected to said recording delay timer whereby said power supply volt meter is released from retaining the value of said power supply voltage at the end of said recording interval.

8. An apparatus as set forth in claim 1 including:
(a) a substantially standard copper-copper sulfate reference electrode having a first terminal thereof connected to said ground in spaced relation to said structure;
(b) said volt meter being connected to a second terminal of said reference electrode whereby said volt meter is connected to said ground by means of said reference electrode; and
(c) said volt meter measuring a structure voltage between said structure and said second terminal of said reference electrode.

9. An apparatus for acquiring data to determine the cathodic protection requirement of a buried metal structure comprising:
(a) power supply means operatively connected to a buried metal structure and the ground in contact with said structure and operative to circulate electrical current therethrough;
(b) current control means operatively connected to said power supply means and operable to set known levels of said current which are circulated;
(c) volt meter means operatively connected between said structure and said ground and operative to measure a structure voltage of said structure relative to said ground corresponding to each level of said circulated current and to releasably retain said structure voltage in response to a voltage hold signal; and
(d) timer means operatively connected to said power supply means and said volt meter means and operative to effect: the circulation of said current during an ON interval of selected duration; the interruption of said circulated current for an OFF interval of selected duration; and the provision of said voltage hold signal to said volt meter means to cause the retention of a structure voltage corresponding to the previously circulated current level at the end of said OFF interval for acquiring a plurality of circulated current levels and corresponding structure voltages for plotting a graph to determine the cathodic protection requirement of said structure in said ground;

(e) said current control means including a stepping relay operative to set each level of said circulated current and to advance to a next level of circulated current after the end of each OFF interval.

10. An apparatus for acquiring data to determine the cathodic protection requirement of a buried metal structure comprising:

(a) power supply means operatively connected to a buried metal structure and the ground in contact with said structure and operative to circulate electrical current therethrough;

(b) current control means operatively connected to said power supply means and operable to set known levels of said current which are circulated;

(c) volt meter means operatively connected between said structure and said ground and operative to measure a structure voltage of said structure relative to said ground corresponding to each level of said circulated current and to releasably retain said structure voltage in response to a voltage hold signal; and (d) timer means operatively connected to said power supply means and said volt meter means and operative to effect: the circulation of said current during an ON interval of selected duration; the interruption of said circulated current for an OFF interval of selected duration; and the provision of said voltage hold signal to said volt meter means to cause the retention of a structure voltage corresponding to the previously circulated current level at the end of said OFF interval for acquiring a plurality of circulated current levels and corresponding structure voltages for plotting a graph to determine the cathodic protection requirements of said structure in said ground; and wherein (e) said timer means includes an ON timer, an OFF timer, and a recording delay timer;

(f) said ON timer is operatively connected to said power supply means and upon activation effects said circulation of said current for said ON interval and the interruption of said current at the end of said ON interval;

(g) said OFF timer is operatively connected to said volt meter means and said ON timer, is activated by said ON timer at the end of said ON interval, and effects the retention of said structure voltage at the end of said OFF interval by providing said voltage hold signal to said volt meter means;

(h) a printer is operatively connected to said volt meter means and said OFF timer and is activated by said OFF timer at the end of said OFF interval to print the value of said structure voltage which is currently retained by said volt meter means;

(i) said current control means includes a stepping relay operative to set each level of said circulated current and to advance to a next level of circulated current in response to a stepper advance signal; and (j) said recording delay timer is operatively connected to said ON timer, said OFF timer, said stepping relay, and said volt meter means and is activated by said OFF timer at the end of a recording interval of selected duration to effect: the activation of said ON timer; the advancement of said stepping relay to the next current level by providing said stepper advance signal thereto; and the release of said volt meter means from retaining the previously measured structure voltage thereby allowing said volt meter means to measure a structure voltage associated with said next current level.

11. An apparatus as set forth in claim 10 including:

(a) a current meter operative to releasably retain the value of said circulated current measured thereby in response to a current hold signal;

(b) an ON delay timer operatively connected between said ON timer and said current meter and operative to provide said current hold signal to said current meter after a selected current hold interval of selected duration after the activation of said ON timer;

(c) said current meter being connected to said printer whereby said printer prints the value of said circulated current which is retained by said current meter during said recording interval; and (d) said current meter being connected to said recording delay timer whereby said current meter is released from retaining said value of circulated current at the end of said recording interval thereby allowing said current meter to measure a next current level.

12. An apparatus as set forth in claim 11 including:

(a) a power supply volt meter connected to said power supply means and said ON delay timer and operative to releasably retain the power supply voltage of said power supply means in response to said current hold signal;

(b) said power supply volt meter being connected to said printer for printing the value of said power supply voltage during said recording interval; and (c) said power supply volt meter being connected to said recording delay timer whereby said power supply volt meter is released from retaining the value of said power supply voltage at the end of said recording interval.

* * * * *